United States Patent
Leclerc et al.

(10) Patent No.: US 9,546,954 B2
(45) Date of Patent: Jan. 17, 2017

(54) ATMOSPHERE PROFILING SYSTEMS

(71) Applicant: Vision Engineering Solutions, LLC, Orlando, FL (US)

(72) Inventors: Troy Leclerc, Sarasota, FL (US); John S Stryjewski, Merritt Island, FL (US)

(73) Assignee: Vision Engineering Solutions, LLC, Orlando, FL (US)

( * ) Notice: Subject to any disclaimer, the term of this patent is extended or adjusted under 35 U.S.C. 154(b) by 0 days.

(21) Appl. No.: 14/886,440

(22) Filed: Oct. 19, 2015

(65) Prior Publication Data

US 2016/0084989 A1    Mar. 24, 2016

Related U.S. Application Data

(63) Continuation of application No. PCT/US2015/050358, filed on Sep. 16, 2015.

(60) Provisional application No. 62/052,015, filed on Sep. 18, 2014.

(51) Int. Cl.
| | | |
|---|---|---|
| *G01N 21/00* | (2006.01) | |
| *G01N 21/59* | (2006.01) | |
| *G01N 21/53* | (2006.01) | |
| *G01W 1/08* | (2006.01) | |
| *G01N 21/17* | (2006.01) | |

(52) U.S. Cl.
CPC ............ *G01N 21/59* (2013.01); *G01N 21/538* (2013.01); *G01W 1/08* (2013.01); *G01N 2021/1793* (2013.01)

(58) Field of Classification Search
CPC ......... G01W 1/00; G01N 21/59; G01N 21/64; G01N 21/68; G01N 2015/1037; G01J 3/03
USPC ...................................... 356/72–73
See application file for complete search history.

(56) References Cited

U.S. PATENT DOCUMENTS

| | | | |
|---|---|---|---|
| 2004/0075605 | A1 | 4/2004 | Bradford et al. |
| 2007/0125910 | A1 | 6/2007 | Cepollina et al. |
| 2007/0171397 | A1 | 7/2007 | Halldorsson et al. |
| 2009/0015460 | A1 | 1/2009 | Fox et al. |
| 2009/0278353 | A1 | 11/2009 | Da Costa Duarte Pardal et al. |
| 2010/0052978 | A1 | 3/2010 | Tillotson |
| 2010/0198514 | A1 | 8/2010 | Miralles |
| 2013/0176570 | A1* | 7/2013 | Beck ................... G01N 21/314 356/433 |

OTHER PUBLICATIONS

Mayer, Kenneth J., "Effect of Inner Scale Atomospheric Spectrum Models on Scintillation in All Optical Turbulence Regimes" Thesis Paper—Spring Term 2007; pp. 1-223.
Andrews, Larry C., et al. "Laser Beam Propagation through Random Media" (2nd edition); pp. 195, 73-74, 481, 483, and 341.
PCT International Search Report and Written Opinion completed by the ISA US on Nov. 2, 2015 and issued in connection with PCT/US2015/050358.

* cited by examiner

*Primary Examiner* — Abdullahi Nur
(74) *Attorney, Agent, or Firm* — Barnes & Thornburg LLP

(57) ABSTRACT

An atmosphere profiling system is disclosed. The atmosphere profiling system is configured to characterize optical properties of the atmosphere.

20 Claims, 2 Drawing Sheets

ATMOSPHERE PROFILING SYSTEMS

This is a continuation of International Application PCT/US15/50358, with an international filing date of 16 Sep. 2015, which claims the benefit of and priority to U.S. Provisional Patent Application No. 62/052,015 filed 18 Sep. 2014, each of which is now expressly incorporated herein by reference.

FIELD OF THE DISCLOSURE

The present disclosure relates generally to atmosphere profiling systems, and more specifically to atmosphere profiling systems for characterizing the optical properties of the atmosphere.

BACKGROUND

Properties of the atmosphere may vary by location and time. For example, optical turbulence and transmission of the atmosphere may vary by location in three-dimensional space. Additionally, the optical turbulence and transmission of the atmosphere at a static point may vary over time.

Transmission may refer to the absorption and scattering of electromagnetic waves such as, for example, visible light. Absorption and scattering of electromagnetic waves may also be called extinction and may be caused by dust and gases in the atmosphere. Optical turbulence may refer to the change in direction of electromagnetic waves as they travel through medium(s) with varying index of refraction. Optical turbulence may be caused by temperature variations in the atmosphere. For example, an object located beyond hot pavement may appear distorted due to the optical turbulence of the atmosphere.

The optical turbulence and transmission properties of the atmosphere may affect the accuracy and/or effectiveness of optical devices such as, for example, laser weapons and other laser devices. As such, an atmosphere profiling system is desired.

SUMMARY

The present disclosure may comprise one or more of the following features and combinations thereof and the claims appended hereto.

An illustrative atmosphere profiling system for characterizing optical properties of the atmosphere is disclosed herein.

The illustrative atmosphere profiling system for characterizing optical properties of the atmosphere may comprise a base platform, an airborne platform configured to move in the atmosphere along a flight path relative to the base platform, the airborne platform arranged to move selectively in three dimensions and to remain in a fixed position relative to the base platform, and a transmitter-reflector system configured to measure optical properties of the atmosphere along the flight path of the airborne platform.

Illustratively, the transmitter-reflector system is connected to the base platform and to the airborne platform and the transmitter-reflector system includes a beacon configured to transmit an optical beam and an optical receiver configured to receive the optical beam.

Illustratively, the beacon is coupled to the airborne platform, the optical receiver is coupled to the base platform, and the flight path corresponds to a trajectory of one or more of a laser and a laser weapon.

In some embodiments, the beacon comprises one or more of a laser diode, an incandescent light, a neon light, a xenon light, a light emitting diode (LED), and a laser beacon.

Illustratively, the atmosphere profiling system further comprises a control station configured to receive data from the transmitter-reflector system and to determine information indicative of a three-dimensional profile of the optical properties of the atmosphere based on the data received from the transmitter-reflector system.

In some embodiments, the atmosphere profiling system includes one or more of a single-aperture scintillometer, a multi-aperture scintillometer, a Differential IMage Motion (DIMM) system, and a wavefront sensor configured to measure atmospheric turbulence.

In some embodiments, the atmosphere profiling system further includes multiple airborne platforms.

In some embodiments, the atmosphere profiling system further includes multiple base platforms.

Also provided is an illustrative method of using the illustrative atmosphere profiling system according to any of the illustrative embodiments disclosed herein. The method may comprise the steps of moving an airborne platform away from a base platform to a first location in the atmosphere, transmitting a first optical beam between the airborne platform and the base platform using a transmitter-reflector system, measuring properties of the transmitted first optical beam, and determining data indicative of the optical properties of the atmosphere based on the measured properties of the transmitted first optical beam.

Illustratively, the transmitter-reflector system includes a beacon configured to transmit the first optical beam and an optical receiver configured to receive the first optical beam and the method further comprises operating a laser weapon based at least in part on the data indicative of the optical properties of the atmosphere.

In some embodiments, the beacon comprises a laser beacon coupled to the base platform, the optical receiver is coupled to the airborne platform, and the method further comprises generating, remotely, a bright spot on the airborne platform with the beacon.

Illustratively, determining data indicative of the optical properties is based on known properties of optical beams emitted by the beacon and the measured properties of the transmitted first optical beam received by the optical receiver.

Illustratively, the method further comprises moving the airborne platform to a second location in the atmosphere, transmitting a second optical beam between the airborne platform and the base platform using the transmitter-reflector system, measuring properties of the transmitted second optical beam, and determining data indicative of a three-dimensional profile of the optical properties of the atmosphere based at least in part on the first optical beam and the second optical beam.

Illustratively, the method further comprises operating a laser weapon based at least in part on the three-dimensional profile.

In some embodiments, the airborne platform includes a video camera and the method further comprises controlling an orientation and motion of the base platform and the airborne platform with video tracking.

Another method of using an atmosphere profiling system may comprise the steps of moving an airborne platform relative to a base platform along a flight path to a first location in the atmosphere, measuring properties of the atmosphere along the flight path, and operating a laser weapon based at least in part on the measured properties of the atmosphere.

Illustratively, the measured properties of the atmosphere include one or more of an atmospheric turbulence, atmospheric extinction, atmospheric scattering, and atmospheric transmission.

Illustratively, the flight path of the airborne platform is indicative of a trajectory of one or more of a laser and a laser weapon.

In some embodiments, the method further comprises determining a distance between the base platform and the airborne platform with a laser ranger and the measured properties of the atmosphere are based at least in part on the distance determined with the laser ranger.

In some embodiments, the method further comprises maintaining the airborne platform in a substantially fixed position at the first location relative to the base platform and moving the airborne platform relative to the base platform along the flight path to a second location in the atmosphere.

Another embodiment of an atmosphere profiling system for characterizing the optical properties of the atmosphere may comprise a base platform, an airborne platform, and a control station.

In some embodiments, the atmosphere profiling system comprises a beacon and a receiver.

In some embodiments, the airborne platform is an unmanned aerial vehicle (UAV) platform.

In some embodiments, the atmosphere profiling system comprises at least one fixed base platform and at least one airborne platform.

In some embodiments, the atmosphere profiling system comprises multiple base platforms.

In some embodiments, the atmosphere profiling system comprises multiple airborne platforms.

In some embodiments, the atmosphere profiling system comprises multiple base platforms and a single airborne platform.

In some embodiments, the atmosphere profiling system comprises a single base platform and multiple airborne platforms.

In some embodiments, the atmosphere profiling system comprises multiple base platforms and multiple airborne platforms.

In some embodiments, the atmosphere profiling system comprises at least one mobile base platform.

In some embodiments, the atmosphere profiling system comprises multiple mobile base platforms.

In some embodiments, the atmosphere profiling system comprises one or more of an incandescent, neon, and xenon light beacon.

In some embodiments, the atmosphere profiling system comprises one or more of a light emitting diode (LED), laser diode, and laser beacon.

In some embodiments, the atmosphere profiling system comprises multiple beacons and multiple receivers.

In some embodiments, the atmosphere profiling system comprises multiple beacons coupled to the at least one base platform.

In some embodiments, the atmosphere profiling system comprises multiple beacons coupled to the at least one airborne platform.

In some embodiments, the atmosphere profiling system comprises at least one staring receiver.

In some embodiments, the atmosphere profiling system comprises at least one steerable receiver.

In some embodiments, the atmosphere profiling system comprises at least one staring beacon.

In some embodiments, the atmosphere profiling system comprises at least one steerable beacon.

In some embodiments, the atmosphere profiling system comprises a receiver in the at least one base platform.

In some embodiments, the atmosphere profiling system comprises a receiver in the at least one airborne platform.

In some embodiments, the atmosphere profiling system comprises multiple beacons with different wavelengths.

In some embodiments, the atmosphere profiling system comprises multiple beacons with different polarizations.

In some embodiments, the atmosphere profiling system is arranged to measure atmospheric turbulence.

In some embodiments, the atmosphere profiling system comprises a single aperture scintillometer to measure atmospheric turbulence.

In some embodiments, the atmosphere profiling system comprises a multi-aperture scintillometer to measure atmospheric turbulence.

In some embodiments, the atmosphere profiling system comprises a Differential IMage Motion (DIMM) system to measure atmospheric turbulence.

In some embodiments, the atmosphere profiling system comprises a wavefront sensor to measure atmospheric turbulence.

In some embodiments, the atmosphere profiling system is arranged to measure atmospheric transmission.

In some embodiments, the atmosphere profiling system is arranged to measure atmospheric scattering.

In some embodiments, the atmosphere profiling system is arranged to measure atmospheric extinction.

In some embodiments, the atmosphere profiling system comprises a global positioning system (GPS) to determine the location of the at least one base platform and the at least one airborne platform.

In some embodiments, the atmosphere profiling system comprises a differential global positioning system (GPS) to determine the location of the at least one base platform and the at least one airborne platform.

In some embodiments, the atmosphere profiling system comprises a laser ranger to determine the distance between the at least one base platform and the at least one airborne platform.

In some embodiments, the atmosphere profiling system comprises a video camera coupled to the at least one base platform.

In some embodiments, the atmosphere profiling system comprises a video camera coupled to the at least one airborne platform.

In some embodiments, the atmosphere profiling system comprises a control station that includes a computer to control the at least one base platform.

In some embodiments, the atmosphere profiling system comprises a control station that includes a computer to control the at least one airborne platform.

In some embodiments, the atmosphere profiling system comprises a control station that can display the video from the at least one base platform and the at least one airborne platform.

In some embodiments, the atmosphere profiling system comprises a control station that can record the video from the at least one base platform and the at least one airborne platform.

In some embodiments, the atmosphere profiling system comprises video tracking to control the motion of the at least one airborne platform.

In some embodiments, the atmosphere profiling system comprises video tracking to control the orientation of the at least one base platform.

In some embodiments, the beacon includes a laser beam arranged to remotely generate a bright spot on the airborne platform.

In some embodiments, the beacon includes a laser beam arranged to remotely illuminate a retro-reflector included in the airborne platform.

In some embodiments, an intensity of the beacon is modulated.

In some embodiments, an intensity of the beacon is modulated using at least one of a sine wave and a square wave.

Another example of a method of using the illustrative atmosphere profiling system according to any of the embodiments is disclosed herein. The method may comprise the steps of providing a base platform, an airborne platform, and a control station, moving the airborne platform away from the base platform to at least one location in the atmosphere, and collecting, during the flight of the airborne platform, data indicative of the optical properties of the atmosphere.

In some embodiments, the airborne platform is moved along a vertical path.

In some embodiments, the airborne platform is moved to at least a second location in the atmosphere after being moved to the first location.

In some embodiments, the method further comprises the step of transmitting the collected data to the control system.

In some embodiments, the collected data is transmitted to the control system by a data link.

In some embodiments, the method further comprises the step of processing the data, with the control system, to obtain information indicative of a three-dimensional profile of the optical properties of the atmosphere.

These and other features of the present disclosure will become more apparent from the following description of the illustrative embodiments.

DETAILED DESCRIPTION OF THE DRAWINGS

Figure 1:
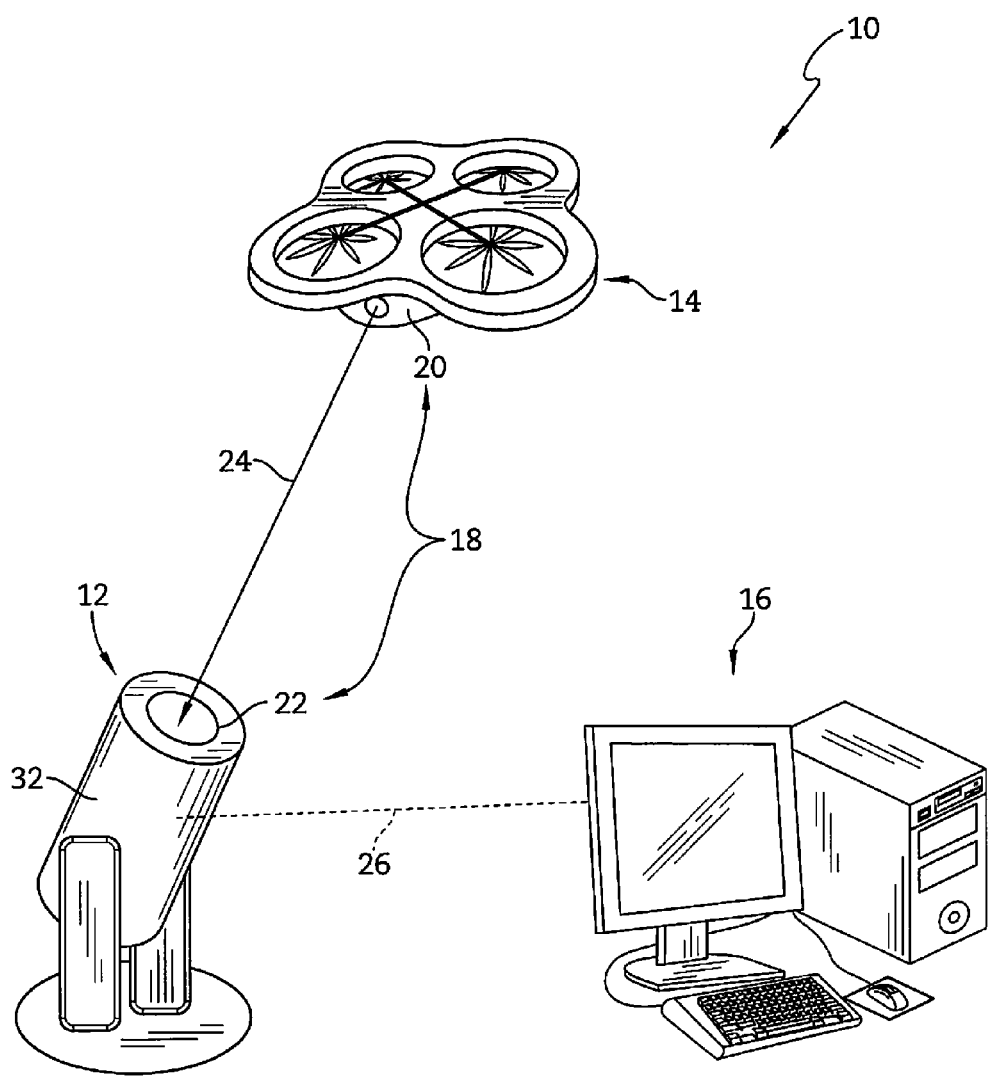
FIG. 1 is a diagrammatic depiction of an illustrative atmosphere profiling system.

For the purposes of promoting an understanding of the principles of the disclosure, reference will now be made to a number of illustrative embodiments illustrated in the drawings and specific language will be used to describe the same.

Referring to FIG. 1, an illustrative atmosphere profiling system 10 is depicted as further described in the Summary and the Claims appended hereto. The atmosphere profiling system 10 is configured to characterize properties of earth's atmosphere. In the illustrative embodiment, the atmosphere profiling system 10 is arranged to characterize the optical turbulence and transmission properties of the atmosphere. The optical turbulence and transmission properties of the atmosphere may affect the accuracy and/or effectiveness of optical devices such as, for example, laser weapons and other laser devices. The characterized properties may be used, for example, to position a laser weapon to maximize the accuracy and/or effectiveness of a beam produced by the laser weapon.

Referring to FIG. 1, the illustrative atmosphere profiling system 10 includes a base platform 12, an airborne platform 14, and a transmitter-reflector system 18. The airborne platform 14 is configured to move relative to the base platform 12. The transmitter-reflector system 18 is arranged to measure the optical properties of a portion of the atmosphere located between the base platform 12 and airborne platform 14. In the illustrative embodiment, a control station 16 controls the base and airborne platforms 12, 14.

In operation, the airborne platform 14 is moved away from the base platform 12 to a first location. Illustratively, the airborne platform 14 is arranged to transmit an optical beam 24 and the base platform 12 is arranged to receive the optical beam 24. The optical properties of the atmosphere such as, for example, transmission and turbulence alter properties of the beam 24 as it travels from the airborne platform 14 to the base platform 12. The altered properties of the beam 24 received at the base platform 12 are compared to the known properties of the beam 24 emitted at the airborne platform 14 to produce data indicative of the optical properties of the atmosphere between the base platform 12 and the first location. The airborne platform 14 may then be moved to a plurality of locations along a flight path and additional data may be collected at discrete points along the flight path.

As a result, the optical properties of the atmosphere along the flight path are obtained. In the illustrative embodiment, the flight path is indicative of a trajectory of a laser weapon. In the illustrative embodiment, the obtained optical properties along the flight path are used to determine/predict the effect of the atmosphere on the accuracy and effectiveness of a beam produced by a high-energy laser weapon.

Referring again to FIG. 1, the atmosphere profiling system 10 includes the base platform 12, the airborne platform 14, and the transmitter-reflector system 18. The transmitter-reflector system 18 is arranged to measure atmospheric properties such as, for example, transmission and turbulence. The control station 16 is arranged to control the base platform 12 and the airborne platform 14. In the illustrative embodiment, the control station 16 is further arranged to record, process, and analyze data received from the base platform 12 and/or airborne platform 14.

In the illustrative embodiment, the transmitter-reflector system 18 includes a beacon 20 and an optical receiver 22. The beacon 20 and the optical receiver 22 are arranged to determine atmospheric properties such as, for example, turbulence and transmission. The beacon 20 may comprise, for example, a laser diode 20. The optical receiver 22 may comprise, for example, a photodiode receiver 22. In some embodiments, the optical receiver 22 is located so as to minimize the effects of the atmospheric turbulence caused by the airborne platform 14 such as, for example, turbulence caused by propellers, if so equipped. As an example, the optical receiver 22 may be located on a boom that extends away from the airborne platform 14 to minimize the effects of atmospheric turbulence.

In the illustrative embodiment, the beacon 20 is included in the airborne platform 14 and the optical receiver 22 is included in the base platform 12. In other embodiments, the beacon 20 is included in the base platform 12 and the optical receiver 22 is included in the airborne platform 14. In the illustrative embodiment, a single beacon 20 is used to measure both transmission and turbulence. In the illustrative embodiment, the airborne platform 14 is a free flying beacon platform. In other embodiments, the airborne platform 14 is a free flying receiver platform.

In some embodiments, the intensity of the beacon 20 is unmodulated. In other embodiments, the intensity of the beacon 20 is modulated. For example, the intensity of the beacon 20 may be modulated using a sine wave, square wave, or any other alternative. In other embodiments, the beacon 20 is implemented by using a laser beam to remotely generate a bright spot on the airborne platform 14. In other embodiments, the beacon 20 is implemented by using a laser beam to remotely illuminate a retro-reflector on the airborne platform 14.

Illustratively, the base platform 12 provides the reference position of the flight path of the airborne platform 14. In other words, the collected atmosphere profile data is referenced from the position of the base platform 12. As such, the base platform 12 may be located, for example, at the origin of a trajectory for weapons.

In the illustrative embodiment, the base platform 12 is located at the origin of a high-energy laser weapon having an approximately straight-line trajectory. The airborne platform 14 is arranged to move from the base platform 12 along the straight-line trajectory to provide atmosphere properties along a path of a beam produced by the high-energy laser weapon. In some embodiments, the base platform 12 may remain stationary relative to earth. In other embodiments, such as, for example, when the base is positioned on a vehicle, the base platform 12 may move relative to earth.

In other embodiments, the base platform 12 is located at an origin of a curved trajectory such as, for example, a trajectory of a mortar-type weapon. In other embodiments, the base platform 12 is positioned at the origin of a rail gun trajectory. In other embodiments, the base platform 12 is positioned at the origin of a designated area having historical measurement interest such as, for example, an airport. For example, the optical properties along a vertical path at the designated area may be recorded each day to obtain a log of historic optical properties. In other embodiments, the base platform 12 is moved between a plurality of locations. In some embodiments, the base platform 12 may be assembled, disassembled, moved from a first location to a second location, and reassembled in about a quarter of an hour to about 24 hours.

In the illustrative embodiment, the base platform 12 includes a mount 32 and the photodiode receiver 22. The photodiode receiver 22 is coupled to the mount 32. The control station 16 is arranged to orient the base platform 12 relative to earth. More particularly, in the illustrative embodiment, the control station 16 is arranged to orient the mount 32 to direct the photodiode receiver 22 toward the LED diode 20 coupled to the airborne platform 14.

The airborne platform 14 is configured to move in the atmosphere relative to the base platform 12. In the illustrative embodiment, the airborne platform 14 is arranged to move in both the vertical and horizontal directions relative to the base platform 12. In other embodiments, the airborne platform 14 moves in only one of the vertical or horizontal directions relative to the base platform 12. The movement of the airborne platform 14 is illustratively controlled by the control station 16. In the illustrative embodiment, the airborne platform 14 is an unmanned aerial vehicle (UAV). In other embodiments, the airborne platform 14 may be, for example, a manned aerial vehicle, a weather balloon, or any other suitable alternative.

The control station 16 controls the base platform 12 and the airborne platform 14. In the illustrative embodiment, the control station 16 communicates with the base platform 12 and the airborne platform 14 via radio waves. In other embodiments, the control station 16 communicates with the base platform 12 and the airborne platform 14 via alternative electromagnetic waves.

The collected data is transmitted to the control station 16 as suggested in FIG. 1. In the illustrative embodiment, the base platform 12 transmits data to the control station 16 via a data link 26 as shown in FIG. 1. In other embodiments, the airborne platform 14 transmits data to the control station 16 via the data link 26. The data link 26 may be a wired or wireless communications link. In some embodiments, the data link 26 comprises Ethernet. In some embodiments, the data link 26 comprises a universal serial bus (USB). In some embodiments, the data link 26 is Link 11. In some embodiments, the data link 26 is Link 16. In some embodiments, the data link 26 is Link 22. In some embodiments, the data link 26 is included in the beacon 20 and the data is transmitted from the beacon 20 to the control station 16 via the beam 24.

It is also within the scope of the disclosure for the airborne platform 14 to carry a plurality of instruments. For example, the airborne platform 14 may include one or more of a thermometer, an altimeter, a hygrometer, a scintillometer, a beacon, a receiver, an interferometer, a meteorology package, a camera, and an air density meter. As such, the atmosphere profiling system 10 may measure and determine a plurality of atmosphere parameters along the flight path. For example, the atmosphere profiling system 10 may measure and determine, among other properties, the temperature, altitude of the airborne platform 14, a distance between the airborne platform 14 and the base platform 12, humidity, air density, air pressure, and solar radiation properties. In other embodiments, the airborne platform 14 provides video feedback and may be used, for example, for control purposes or for surveillance purposes.

In some embodiments, the airborne platform 14 is in communication with a satellite. In some embodiments, the airborne platform 14 includes a Global Positioning System (GPS). In some embodiments, the base platform 12 includes a Global Positioning System (GPS). In some embodiments, the atmosphere profiling system 10 uses Geodetic Information System (GIS) data to determine the ground altitude profile of the area under measurement.

In some embodiments, the atmosphere profiling system 10 includes a plurality of base platforms 12. In some embodiments, the base platforms 12 are in communication with each other. In some embodiments, the atmosphere profiling system 10 includes a plurality of UAV platforms 14. In some embodiments, the UAV platforms 14 are in communication with each other. In some embodiments, the base platform 12 is in communication with a satellite.

In some embodiments, the atmosphere profiling system comprises at least one staring receiver. In some embodiments, the atmosphere profiling system comprises at least one steerable receiver. In some embodiments, the atmosphere profiling system comprises at least one staring beacon. In some embodiments, the atmosphere profiling system comprises at least one steerable beacon. In some embodiments, the measured properties of the atmosphere along the flight path include one or more of an atmospheric turbulence, atmospheric extinction, atmospheric scattering, and atmospheric transmission.

Illustratively, the beacon 20 of the airborne platform 14 is arranged to transmit the optical beam 24 and the photodiode receiver 22 included in the base platform 12 is arranged to receive the optical beam 24. The optical properties of the atmosphere such as, for example, transmission and turbulence alter properties of the beam 24 as it travels from the beacon 20 to the photodiode receiver 22.

The base platform 12 compares the altered properties of the beam 24 to the known properties of the beam 24 at the airborne platform 14 to produce data indicative of the optical properties of the atmosphere between the base platform 12 and the airborne platform 14. The airborne platform 14 may be moved to a single position or it may be moved to a plurality of locations along a flight path and additional data may be collected at discrete points along the flight path.

In the illustrative embodiment, the atmosphere is sampled at about 1000 hertz. In other embodiments, the atmosphere is sampled between about 2 hertz and about 20,000 hertz. In some embodiments, the airborne platform 14 travels along the flight path in about one minute. As an example, the airborne platform 14 travels a distance equal to the extreme operating range of a laser weapon in about one minute.

In the illustrative embodiment, transmission is measured using a known output power of the beacon 20 and a known sensitivity of the optical receiver 22. In the illustrative embodiment, turbulence is measured using a multi-aperture scintillometer. In other embodiments, the turbulence is measured using a single aperture scintillometer.

The turbulence measurement is used with an atmospheric propagation model to determine a path averaged refractive index structure parameter, $C_n^2$, a path averaged inner scale, $l_0$, and a path averaged outer scale, $L_0$, for the beam 24 path. By moving the airborne platform 14 along a number of flight paths and using a physical model, a three-dimensional map of the refractive index structure parameter, the inner scale, and the outer scale of the atmosphere is developed. In some embodiments, the Hufnagle-Andrews-Phillips (HAP) model for the atmosphere is used. In other embodiments, other path averaged atmospheric optical properties such as, for example, coherence radius, beam angle of arrival statistics, or wavefront distortion are measured to characterize the atmosphere.

One method of characterizing the effects of the atmosphere turbulence on laser beams, imaging systems, and other optical devices includes calculating the Wave Structure Function (WSF) or a quantity derived from the Wave Structure Function. The Wave Structure Function is calculated by integrating the atmospheric effects along the propagation path. As an example, from the book "Laser Beam Propagation Through Random Media" by Larry Andrews and Ron Phillips, the Wave Structure Function for a spherical wave may be given by the following path integral:

$$D(\rho, L) = 8\pi^2 k^2 L \int_0^1 \int_0^\infty \kappa \phi(\kappa, \xi)(1 - J_0(\kappa \xi \rho)) d\kappa d\xi \quad \text{Equation 1}$$

Once the path integral $D(\rho,L)$ is determined, other quantities such as, for example, the Scintillation index and coherence radius may be calculated. The Wave Structure Function includes the spectral function $\Phi(\kappa,\xi)$ which embodies the effects of the turbulent atmosphere on the propagating wavefront. The spectral function is generally approximated by one of several expressions:

$$\Phi(\kappa) = 0.033 C_n^2 \kappa^{-\frac{11}{3}} \quad \text{Equation 2}$$

(Kolmogorov Spectra)

$$\Phi(\kappa) = 0.033 C_n^2 \kappa^{-\frac{11}{3}} \exp\left(-\frac{\kappa^2}{\kappa_m^2}\right), \kappa_m = \frac{5.92}{l_o} \quad \text{Equation 3}$$

(Tatarskii Spectra)

-continued $$\Phi(\kappa) = 0.033 C_n^2 \left[1 + 1.802\left(\frac{\kappa}{\kappa_l}\right) - 0.254\left(\frac{\kappa}{\kappa_l}\right)^{\frac{7}{6}}\right] \frac{\exp\left(\frac{\kappa^2}{\kappa_l}\right)}{(\kappa^2 + \kappa_0^2)^{\frac{11}{6}}}, \quad \text{Equation 4}$$

$$\kappa_l = \frac{3.3}{l_o}, \kappa_0 = \frac{2\pi}{L_0}$$

(Mod. Spectra)

$$\Phi(\kappa) = 0.033 C_n^2 \kappa^{-\frac{11}{3}} \left[\frac{7}{5} \exp\left(-\frac{(\kappa - \kappa_m)^2}{\kappa_m^2}\right)\right], \kappa_m = \frac{1.496}{l_0} \quad \text{Equation 5}$$

(Exponential Approximation)

In other embodiments, the spectral function may be approximated by one or more other expressions. These approximations relate the spectral function $\Phi(\kappa,\xi)$ to the atmospheric structure constants $C_n^2$, and optionally two scale constants, $l_0$ and $L_0$. Some methods of measuring atmospheric turbulence assume these quantities to be constants. However, they may be generally dependent on altitude above the ground, weather, and local terrain. As a result, to characterize the atmosphere, the spatial dependence of these quantities may be measured so that the laser or imaging path integral can be reconstructed.

In the illustrative embodiment, the measurements are restricted to about two to three times the Atmospheric Boundary Layer (ABL) or altitudes of less than three to five kilometers. In the illustrative embodiment, the Hufnagle-Andrews-Phillips (HAP) model for the atmosphere is assumed and we model $C_n^2$ as:

$$C_n^2(x, y, h) = (2.7 \times 10^{-16}) \exp\left(-\frac{h}{1500}\right) + \quad \text{Equation 6}$$

$$\text{Function}(x, y)\left(\frac{h}{h_o}\right)^{-4/3}, alt < 5 \text{ km}$$

with, $$l_0 = \frac{4 \text{ mm}}{1 + \left(\frac{h - 7500}{2500}\right)^2} \cdot \text{Function}(x, y) \quad \text{Equation 7}$$

and $$L_0 = (0.5 \text{ m} + h) \cdot \text{Function}(x, y) \quad \text{Equation 8}$$

Here, x and y may be latitude and longitude and h may be altitude. These functions may be used to calculate $\Phi(x,y,z,\kappa)$, which may then be used to calculate a measurable path integral quantity such as, for example, Scintillation Index (SI):

$$\sigma_{lnl}^2 = 8\pi^2 k^2 \int_0^L \int_0^\infty \kappa \Phi(x, y, z, \kappa)\left(1 - \cos\left(\frac{\kappa^2}{\kappa}z\left(1 - \frac{z}{L}\right)\right)\right) d\kappa dz \quad \text{Equation 9}$$

By making many 3D measurements of the Scintillation index, the free parameters in the models for the atmospheric intrinsic properties may be determined, (equation 6). Once the model is determined, any path integral of quantity of interest may be calculated.

Figure 2:
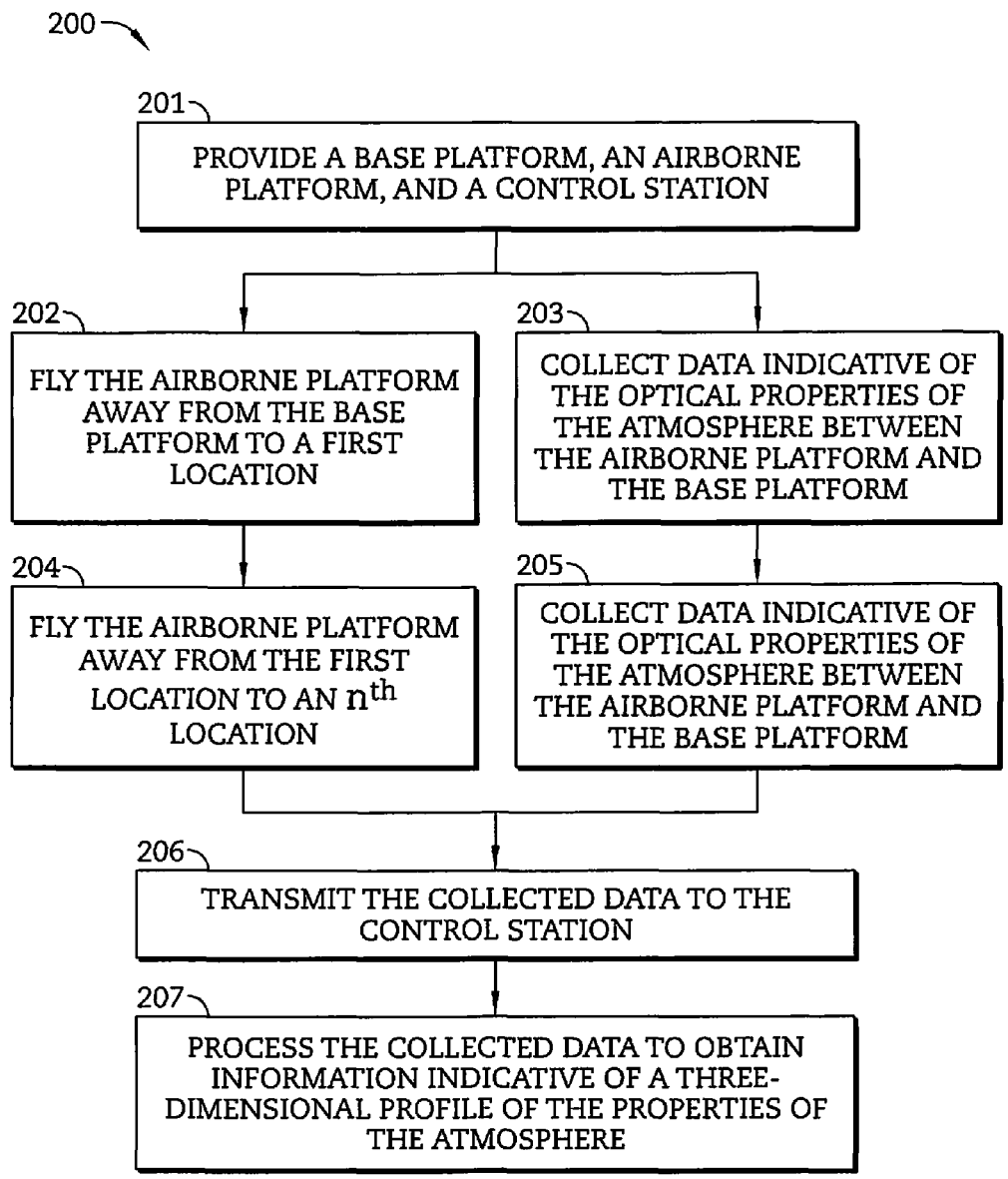
FIG. 2 is a diagrammatic depiction of a method of using the illustrative atmosphere profiling system.

An illustrative method 200 of using the atmosphere profiling system 10 includes a number of steps as shown in FIG. 2. In a step 201, the base platform 12, the airborne platform 14, and the control station 16 are provided.

In a step 202, the airborne platform 14 is moved away from the base platform 12 along a first flight path to a first location in the atmosphere to collect data. In some embodiments, the airborne platform 14 communicates with the base platform 12 at an altitude between about zero and about 20,000 meters vertically above the base platform 12. In some embodiments, the airborne platform 14 communicates with the base platform 12 at an altitude between 0 meters and about 4,000 meters above the base platform 12. In the illustrative embodiment, the airborne platform 14 communicates with the base platform 12 at an altitude equal to or less than about 1,000 meters above the base platform 12. The flight path of the airborne platform 14 may be vertical, horizontal, along a slanted path, or any other suitable alternative.

In a step 203, data indicative of the optical properties of the atmosphere between the base platform 12 and the airborne platform 14 is collected. In the illustrative embodiment, the beacon 20 included in the airborne platform 14 produces an electromagnetic wave 24, illustratively a laser beam 24. The beam 24 is transmitted to the optical receiver 22 included in the base platform 12. Atmospheric parameters are determined using values of the beacon 20, the receiver 22, and the electromagnetic wave 24 detected at the receiver 22. The atmospheric parameters are collected continuously during the moving step 202.

In a step 204, the airborne platform 14 is moved away from the first location along an $n^{th}$ flight path to an $n^{th}$ location in the atmosphere. The flight path of the airborne platform 14 may be vertical, horizontal, along a slanted path, or any other suitable alternative. In other embodiments, the airborne platform 14 returns to the base platform 12 before moving to the $n^{th}$ location in the atmosphere. In the illustrative embodiment, the parameters are measured along multiple propagation paths to obtain a vertical and/or horizontal profile of the atmosphere. In some embodiments, the airborne platform 14 is moved along paths with varying ranges from the base platform 12.

In a step 205, data indicative of the optical properties of the atmosphere between the base platform 12 and the airborne platform 14 is collected. Illustratively, the atmospheric parameters are collected continuously during the moving step 204.

In a step 206, the collected data is transmitted to the control station 16. In the illustrative embodiment, the data is transmitted to the control station 16 from the base platform 12 along a data link 26. In other embodiments, the data is transmitted to the control station 16 from the airborne platform 14. In the illustrative embodiment, the collected data is transmitted to the control station 16 as the data is collected. In other embodiments, the collected data is transmitted to the control station from a memory included in the base platform 12 or the airborne platform 14 after all moving steps are completed.

In a step 207, the collected data is processed by the control station 16 to obtain information indicative of a three-dimensional profile of the properties of the atmosphere. In the illustrative embodiment, the collected data is processed as the data is received by the control station 16. In other embodiments, the collected data is processed after all desired data is transmitted to the control station 16.

Another method 300 of using the atmosphere profiling system 10 includes a number of steps. In a step 301, the airborne platform is moved away from a base platform to a first location in the atmosphere. In a step 302, a first optical beam is transmitted between the airborne platform and the base platform using a transmitter-reflector system. In a step 303, the properties of the transmitted first optical beam are measured. In a step 304, data indicative of the optical properties of the atmosphere based on the measured properties of the transmitted first optical beam are determined.

In some embodiments, the method further comprises operating a laser weapon based at least in part on the data indicative of the optical properties of the atmosphere.

In some embodiments, the method further comprises moving the airborne platform to a second location in the atmosphere, transmitting a second optical beam between the airborne platform and the base platform using the transmitter-reflector system, measuring properties of the transmitted second optical beam, and determining data indicative of a three-dimensional profile of the optical properties of the atmosphere based at least in part on the first optical beam and the second optical beam.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. An atmosphere profiling system for characterizing optical properties of the atmosphere, the atmosphere profiling system comprising:
   a base platform,
   an airborne platform configured to move in the atmosphere along a flight path relative to the base platform, the airborne platform arranged to move selectively in three dimensions and to remain in a fixed position relative to the base platform, and
   a transmitter-reflector system configured to measure one or more of an atmospheric turbulence, atmospheric extinction, atmospheric scattering, and atmospheric transmission of the atmosphere along the flight path of the airborne platform,
   wherein the atmosphere profiling system includes one or more of a single-aperture scintillometer, a multi-aperture scintillometer, a Differential IMage Motion (DIMM) system, and a wavefront sensor configured to measure the one or more of the atmospheric turbulence, atmospheric extinction, atmospheric scattering, and atmospheric transmission of the atmosphere.

2. The atmosphere profiling system of claim 1, wherein the transmitter-reflector system is connected to the base platform and to the airborne platform and the transmitter-reflector system includes a beacon configured to transmit an optical beam and an optical receiver configured to receive the optical beam.

3. The atmosphere profiling system of claim 2, wherein the beacon is coupled to the airborne platform, the optical receiver is coupled to the base platform, and the flight path corresponds to a trajectory of one or more of a laser and a laser weapon.

4. The atmosphere profiling system of claim 2, wherein the beacon comprises one or more of a laser diode, an incandescent light, a neon light, a xenon light, a light emitting diode (LED), and a laser beacon.

5. The atmosphere profiling system of claim 1, further comprising a control station configured to receive data from the transmitter-reflector system and to determine information indicative of a three-dimensional profile of the optical properties of the atmosphere based on the data received from the transmitter-reflector system.

6. The atmosphere profiling system of claim 5, further including multiple airborne platforms.

7. The atmosphere profiling system of claim 5, further including multiple base platforms.

8. A method of using an atmosphere profiling system, the method comprising the steps of: moving an airborne platform away from a base platform to a first location in the atmosphere, transmitting a first optical beam between the airborne platform and the base platform using a transmitter-reflector system, measuring properties of the transmitted first optical beam, and determining data indicative of the optical properties of the atmosphere based on the measured properties of the transmitted first optical beam, wherein determining data indicative of the optical properties of the atmosphere includes determining one or more of an atmospheric turbulence, atmospheric extinction, atmospheric scattering, and atmospheric transmission, wherein the atmosphere profiling system includes one or more of a single-aperture scintillometer, a multi-aperture scintillometer, a Differential IMage Motion (DIMM) system, and a wavefront sensor configured to measure the one or more of the atmospheric turbulence, atmospheric extinction, atmospheric scattering, and atmospheric transmission of the atmosphere.

9. The method of claim 8, wherein the transmitter-reflector system includes a beacon configured to transmit the first optical beam and an optical receiver configured to receive the first optical beam and the method further comprises operating a laser weapon based at least in part on the data indicative of the optical properties of the atmosphere.

10. The method of claim 9, wherein the beacon comprises a laser beacon coupled to the base platform, the optical receiver is coupled to the airborne platform, and the method further comprises generating, remotely, a bright spot on the airborne platform with the beacon.

11. The method of claim 9, wherein determining data indicative of the optical properties is based on known properties of optical beams emitted by the beacon and the measured properties of the transmitted first optical beam received by the optical receiver.

12. The method of claim 8, further comprising moving the airborne platform to a second location in the atmosphere, transmitting a second optical beam between the airborne platform and the base platform using the transmitter-reflector system, measuring properties of the transmitted second optical beam, and determining data indicative of a three-dimensional profile of the optical properties of the atmosphere based at least in part on the first optical beam and the second optical beam.

13. The method of claim 12, further comprising operating a laser weapon based at least in part on the three-dimensional profile.

14. The method of claim 12, wherein the airborne platform includes a video camera and the method further comprises controlling an orientation and motion of the base platform and the airborne platform with video tracking.

15. The method of claim 8, further comprising determining a distance between the base platform and the airborne platform and providing a profile of the one or more of the atmospheric turbulence, atmospheric extinction, atmospheric scattering, and atmospheric transmission based on the data indicative of the optical properties of the atmosphere and the distance between the base platform and the airborne platform.

16. A method of using an atmosphere profiling system, the method comprising the steps of: moving an airborne platform relative to a base platform along a flight path to a first location in the atmosphere, measuring properties of the atmosphere along the flight path, and operating a laser weapon based at least in part on the measured properties of the atmosphere, wherein the measured properties of the atmosphere include one or more of an atmospheric turbulence, atmospheric extinction, atmospheric scattering, and atmospheric transmission, wherein the atmosphere profiling system includes one or more of a single-aperture scintillometer, a multi-aperture scintillometer, a Differential IMage Motion (DIMM) system, and a wavefront sensor configured to measure the one or more of the atmospheric turbulence, atmospheric extinction, atmospheric scattering, and atmospheric transmission of the atmosphere.

17. The method of claim 16, wherein the flight path of the airborne platform is indicative of a trajectory of one or more of a laser and a laser weapon.

18. The method of claim 16, further comprising determining a distance between the base platform and the airborne platform with a laser ranger and the measured properties of the atmosphere are based at least in part on the distance determined with the laser ranger.

19. The method of claim 16, further comprising maintaining the airborne platform in a substantially fixed position at the first location relative to the base platform and moving the airborne platform relative to the base platform along the flight path to a second location in the atmosphere.

20. The method of claim 16, further comprising determining a three-dimensional position of the airborne platform and providing a three-dimensional profile of the optical properties of the atmosphere based on the measured properties of the atmosphere and the three-dimensional position of the airborne platform.

* * * * *